United States Patent
Dae et al.

(10) Patent No.: US 10,369,044 B2
(45) Date of Patent: *Aug. 6, 2019

(54) INHIBITION OF PLATELET ACTIVATION, AGGREGATION AND/OR ADHESION BY HYPOTHERMIA

(71) Applicant: ZOLL Circulation Inc., San Jose, CA (US)

(72) Inventors: Michael W. Dae, Belmont, CA (US); Timothy R. Machold, Moss Beach, CA (US); Wade A. Keller, San Jose, CA (US)

(73) Assignee: ZOLL Circulation, Inc., San Jose, CA (US)

( * ) Notice: Subject to any disclaimer, the term of this patent is extended or adjusted under 35 U.S.C. 154(b) by 378 days.

This patent is subject to a terminal disclaimer.

(21) Appl. No.: 15/174,690

(22) Filed: Jun. 6, 2016

(65) Prior Publication Data

US 2016/0354236 A1    Dec. 8, 2016

Related U.S. Application Data

(63) Continuation of application No. 13/868,764, filed on Apr. 23, 2013, now Pat. No. 9,358,153, which is a (Continued)

(51) Int. Cl.
A61F 7/12    (2006.01)

(52) U.S. Cl.
CPC ............... *A61F 7/12* (2013.01); *A61F 7/123* (2013.01); *A61F 2007/126* (2013.01)

(58) Field of Classification Search
CPC ....... A61F 7/12; A61F 7/123; A61F 2007/126
See application file for complete search history.

(56) References Cited

U.S. PATENT DOCUMENTS 697,181 A    4/1902    Smith
3,425,419 A    2/1969    Dato
(Continued)

FOREIGN PATENT DOCUMENTS

WO    99/18939    4/1999

OTHER PUBLICATIONS

Jessen et al. "Intravascular Heat Exchanger for Conscious Goats," Pflugers Archiv, European Journal of Physiology, / vol. 368. pp. 263-265 1977.

(Continued)

*Primary Examiner* — Kaitlyn E Smith
(74) *Attorney, Agent, or Firm* — Robert D. Buyan; Stout, Uxa & Buyan, LLP

(57) ABSTRACT

A method for treating acute coronary syndromes (i.e., unstable angina or non-Q-wave MI) or transient ischemic attacks in a human or animal patient by placing a heat exchange apparatus in the patient=s vasculature and using that heat exchange apparatus to cool the patient to a temperature (e.g. 30-36 degrees C.) at which platelet inhibition (i.e., inhibition of platelet activation and/or aggregation and/or adhesion) occurs. Anti-shivering drugs or anesthesia may be administered to patients whose body temperature is cooled below that patient=s shivering threshold (typically approximately 35.5 degrees C.). If it is determined that platelet inhibition is no longer desirable, such as when the patient is about to undergo a surgical or interventional procedure wherein bleeding could be problematic, the hypothermia-induced platelet inhibition may be rapidly reversed by using the intravascular heat exchange apparatus to rewarm the patient=s body to normothermia or near normothermia.

19 Claims, 10 Drawing Sheets

Related U.S. Application Data continuation of application No. 12/962,487, filed on Dec. 7, 2010, now Pat. No. 8,425,581, which is a continuation of application No. 11/501,442, filed on Aug. 8, 2006, now Pat. No. 7,846,193, which is a continuation of application No. 10/408,617, filed on Apr. 7, 2003, now abandoned, which is a continuation of application No. 09/790,249, filed on Feb. 21, 2001, now Pat. No. 6,544,282.

(56) References Cited

U.S. PATENT DOCUMENTS

| | | |
|---|---|---|
| 5,174,285 A | 12/1992 | Fontenot |
| 5,344,436 A | 9/1994 | Fontenot et al. |
| 5,486,204 A | 1/1996 | Clifton |
| 5,486,208 A | 1/1996 | Ginsburg |
| 5,837,003 A | 11/1998 | Ginsburg |
| 5,928,181 A | 7/1999 | Coleman et al. |
| 5,957,963 A | 9/1999 | Dobak, III |
| 6,042,559 A | 3/2000 | Dobak, III |
| 6,051,019 A | 4/2000 | Dobak, III |
| 6,096,068 A | 8/2000 | Dobak, III et al. |
| 6,126,684 A | 10/2000 | Gobin et al. |
| 6,146,411 A | 11/2000 | Noda et al. |
| 6,149,670 A | 11/2000 | Worthen et al. |
| 6,149,673 A | 11/2000 | Ginsburg |
| 6,149,676 A | 11/2000 | Ginsburg |
| 6,224,624 B1 | 5/2001 | Lasheras et al. |
| 6,231,594 B1 | 5/2001 | Dae |
| 6,238,428 B1 | 5/2001 | Werneth et al. |
| 6,245,095 B1 | 6/2001 | Dobak, III et al. |
| 6,251,129 B1 | 6/2001 | Dobak, III et al. |
| 6,287,326 B1 | 9/2001 | Pecor |
| 6,299,599 B1 | 10/2001 | Pham et al. |
| 6,379,378 B1 | 4/2002 | Werneth et al. |
| 6,405,080 B1 | 6/2002 | Lasersohn et al. |
| 6,416,533 B1 | 7/2002 | Gobin et al. |
| 6,432,124 B1 | 8/2002 | Worthen et al. |
| 6,436,130 B1 | 8/2002 | Philips et al. |
| 6,447,474 B1 | 9/2002 | Balding |
| 6,454,793 B1 * | 9/2002 | Evans ............ A61F 7/12 128/898 |
| 6,458,150 B1 | 10/2002 | Evans et al. |
| 6,468,296 B1 | 10/2002 | Dobak et al. |
| 6,491,039 B1 | 12/2002 | Dobak, III |
| 6,527,798 B2 | 3/2003 | Ginsburg et al. |
| 6,544,282 B1 | 4/2003 | Dae et al. |
| 6,582,398 B1 | 6/2003 | Worthen et al. |
| 6,610,083 B2 | 8/2003 | Keller |
| 6,620,188 B1 | 9/2003 | Ginsburg |
| 6,673,098 B1 | 1/2004 | Machold et al. |
| 6,843,800 B1 | 1/2005 | Dobak, III |
| 8,425,581 B2 | 4/2013 | Dae et al. |
| 2002/0007202 A1 | 1/2002 | Dobak et al. |
| 2002/0032430 A1 | 3/2002 | Luo et al. |

OTHER PUBLICATIONS

Mercer et al., "Effects of Total Body Core Cooling on Heat Production of Conscious Goats." Pflugers Archiv, European Journal of Physiology, vol. 373, pp. 259-267, 1978.

Michelson et al., "Reversible Inhibition of Human Platelet Activation by Hypothermia in Vivo and in Vitro", Thromb Haemost May 1994, vol. 71(5), pp. 633-640.

Michelson et al, "The Effects of Aspirin and Hypothermia on Platelet Function in Vivo", British Journal of Haematology Jan. 1999, vol. 104(1), pp. 64-68.

Watts, Dorraine Day, "Hypothermia Coagulopathy in Trauma: Effect of Varying Levels of Hypothermia on Enzyme Speed, Platelet Function and Fibrinolytic Activity", 1997, p. 1-10.

Frelinger et al., "Combined Effects of Mild Hypothermia and Glycoprotein IIb//IIIa Antagonists on Platelet-Platelet and Leukocyte-Platelet Aggregation", The American Journal of Cardiology, vol. 92, Nov. 1, 2003.

* cited by examiner

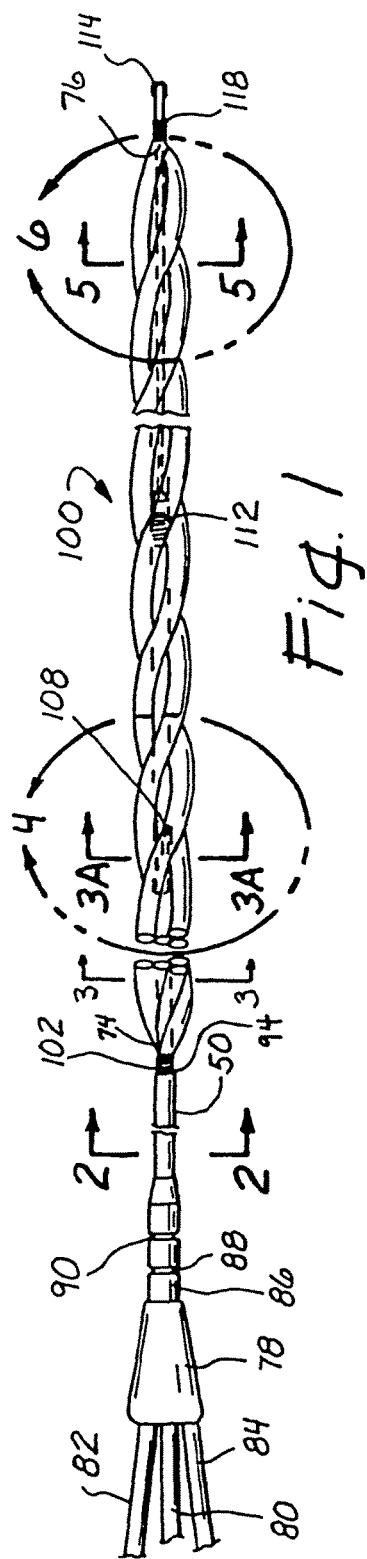
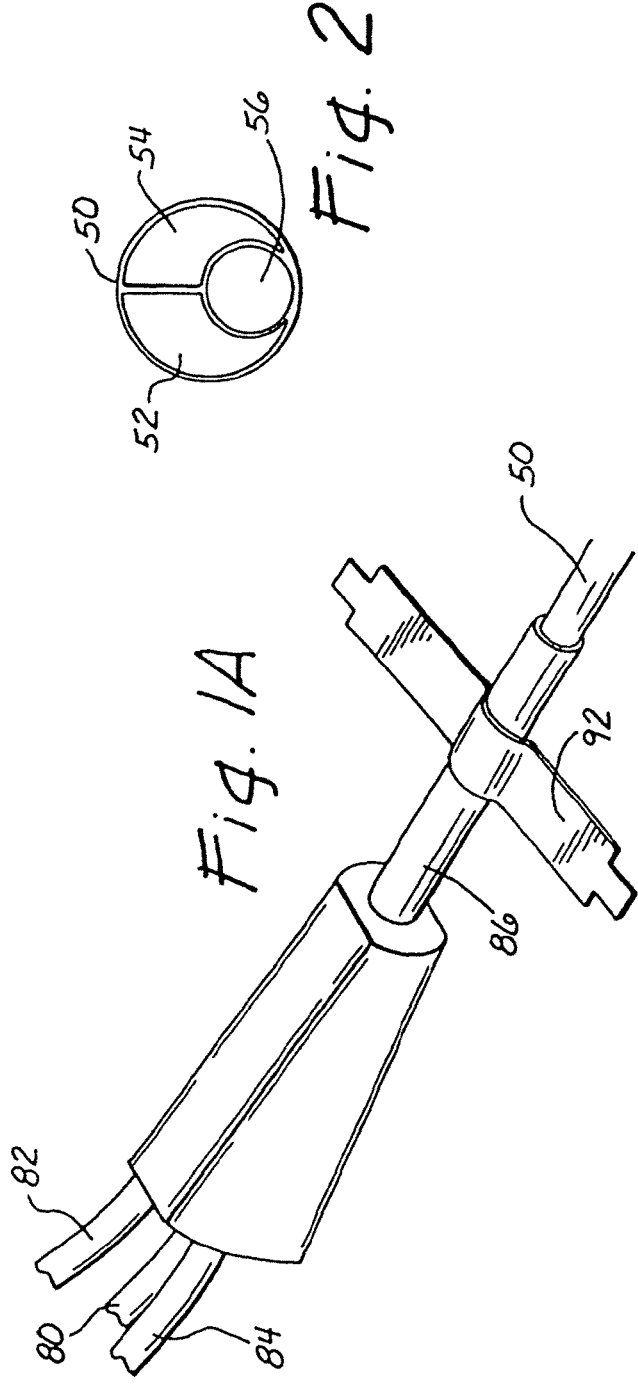

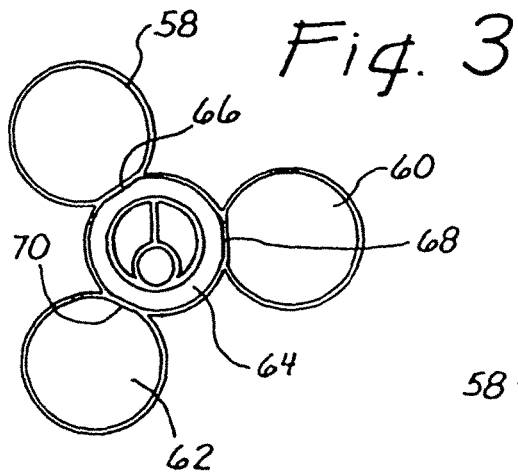
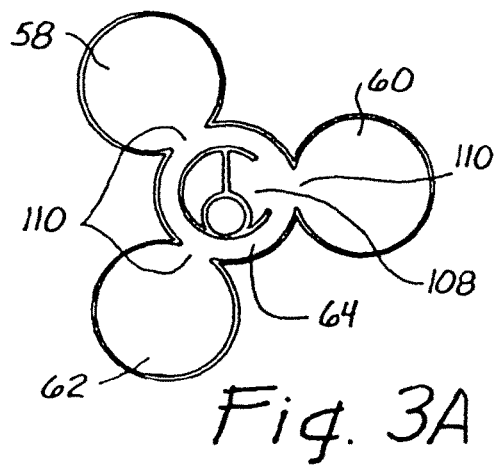
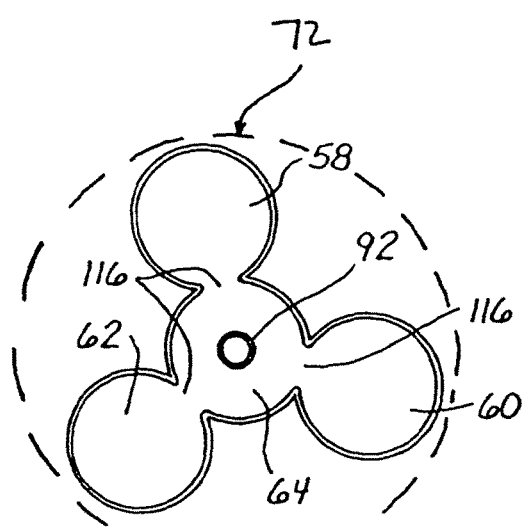
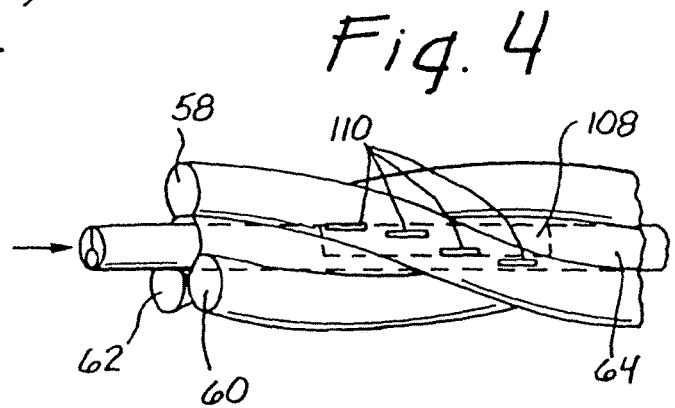

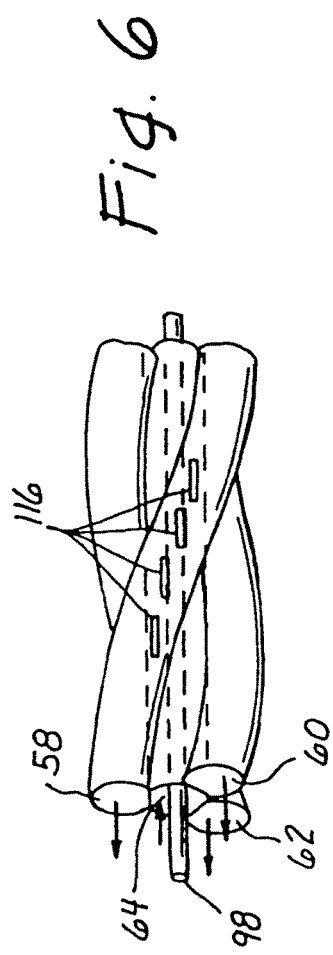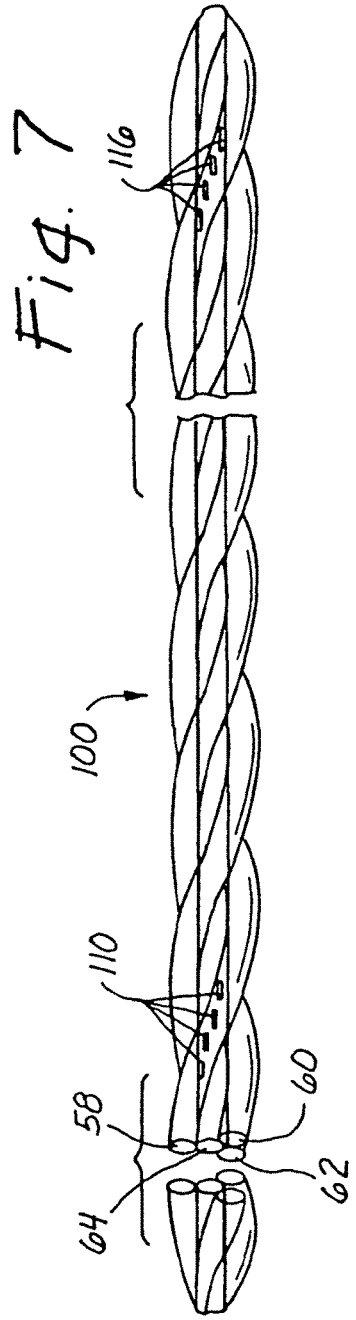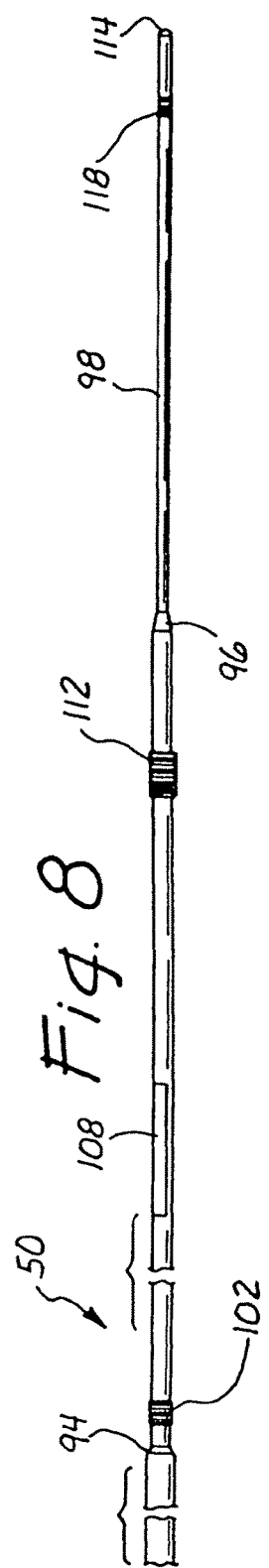

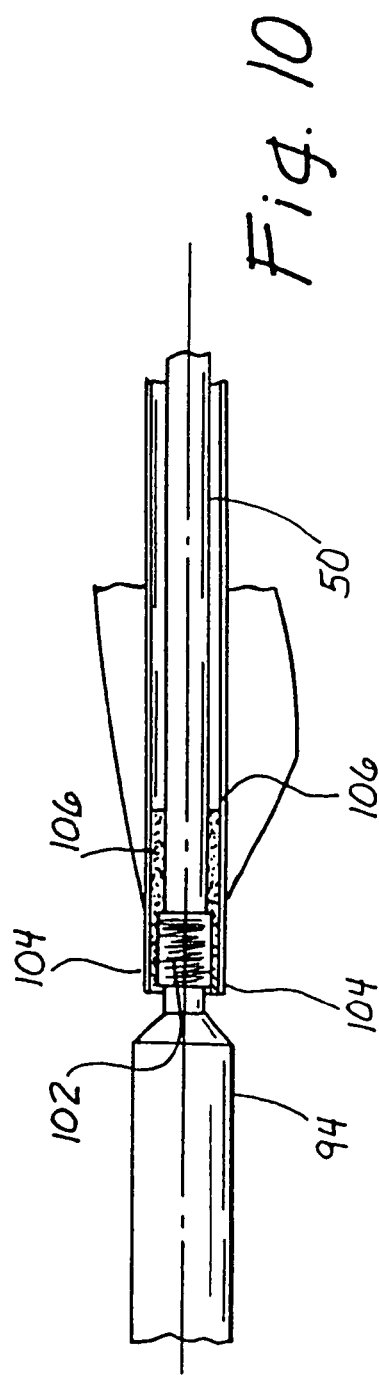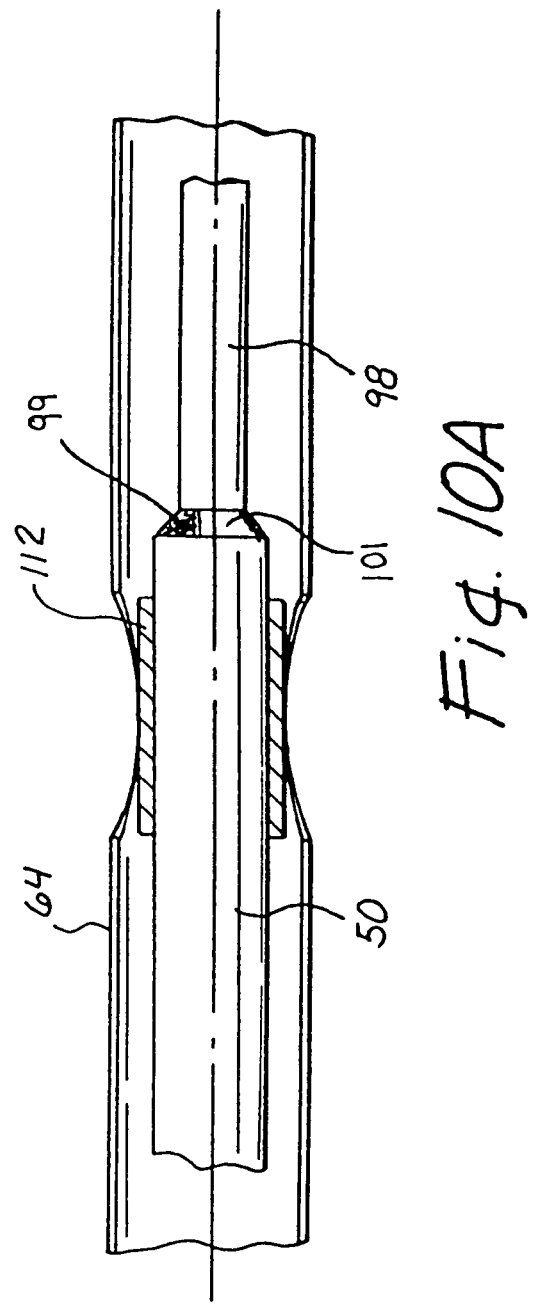

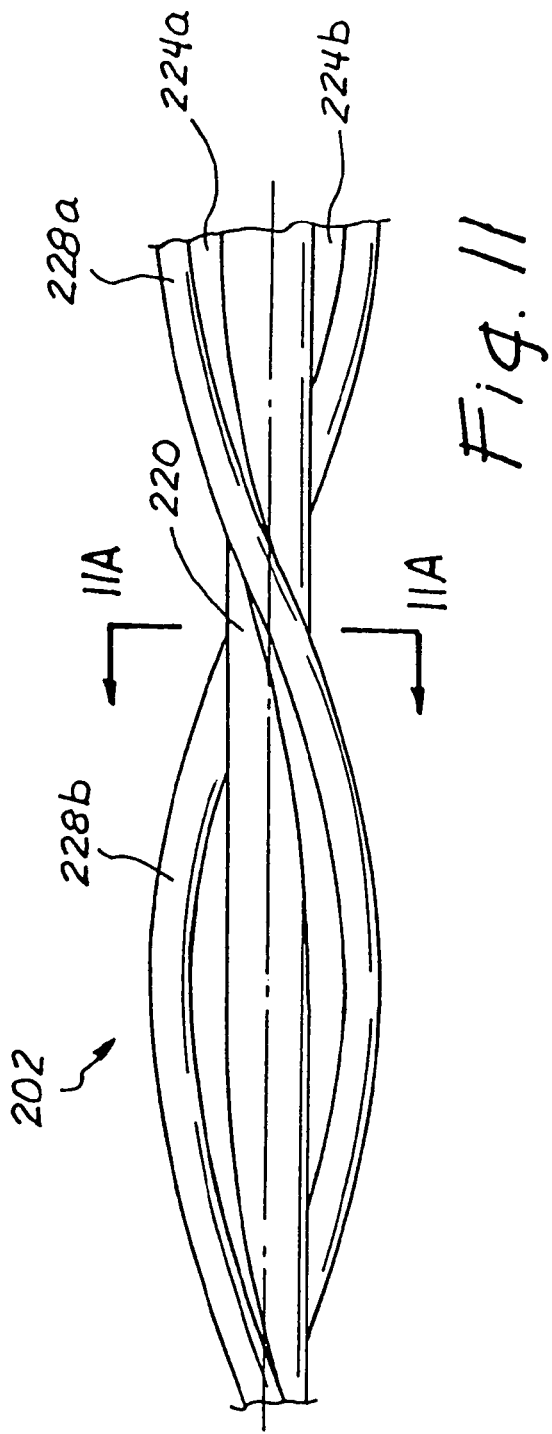
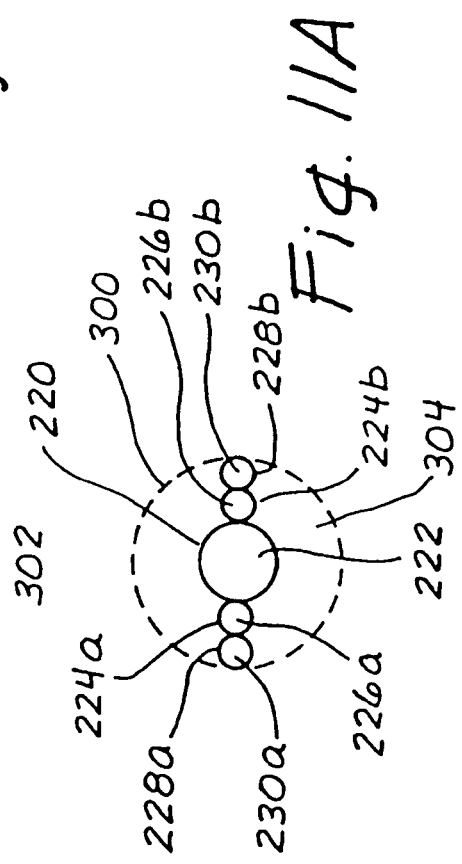

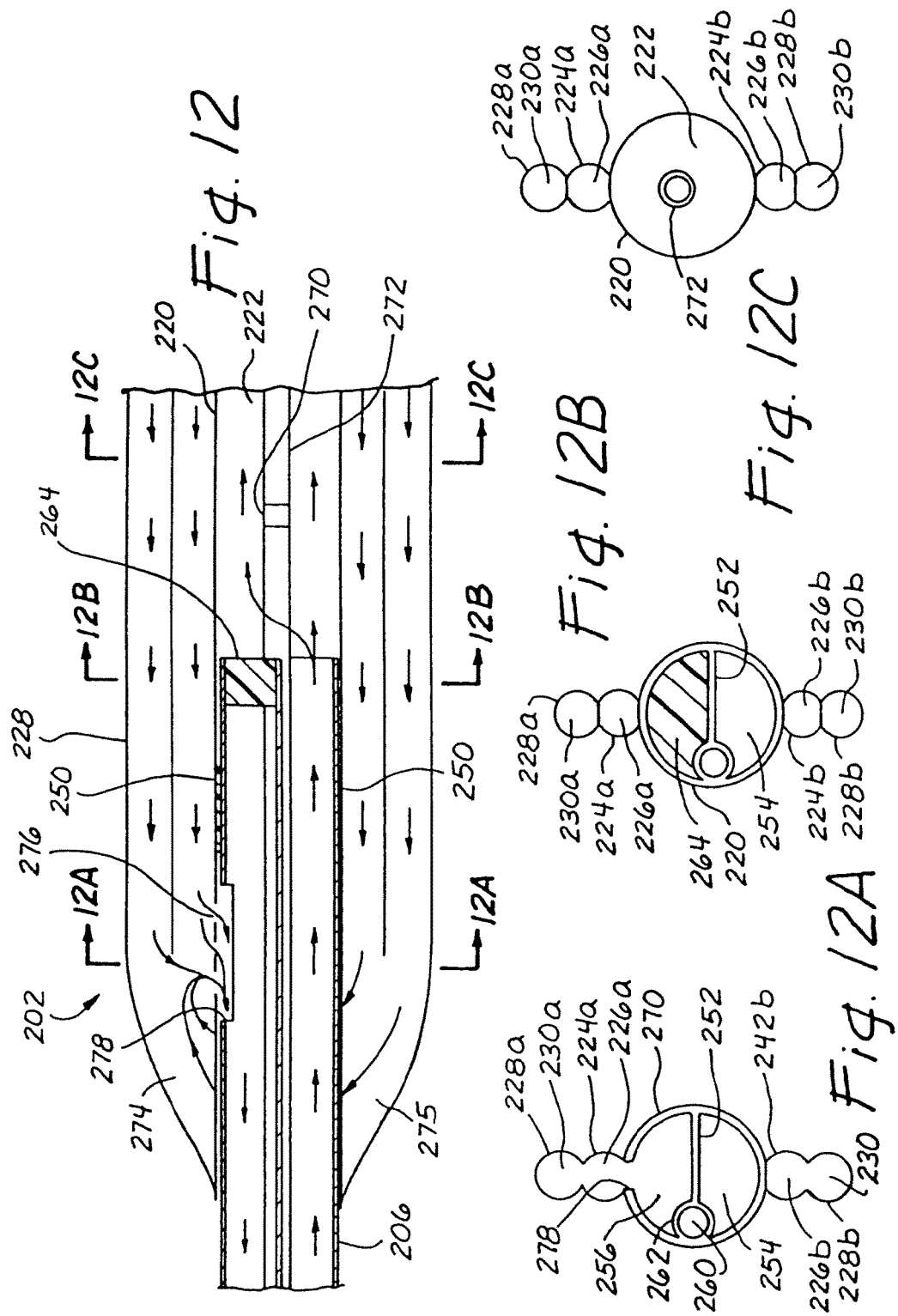

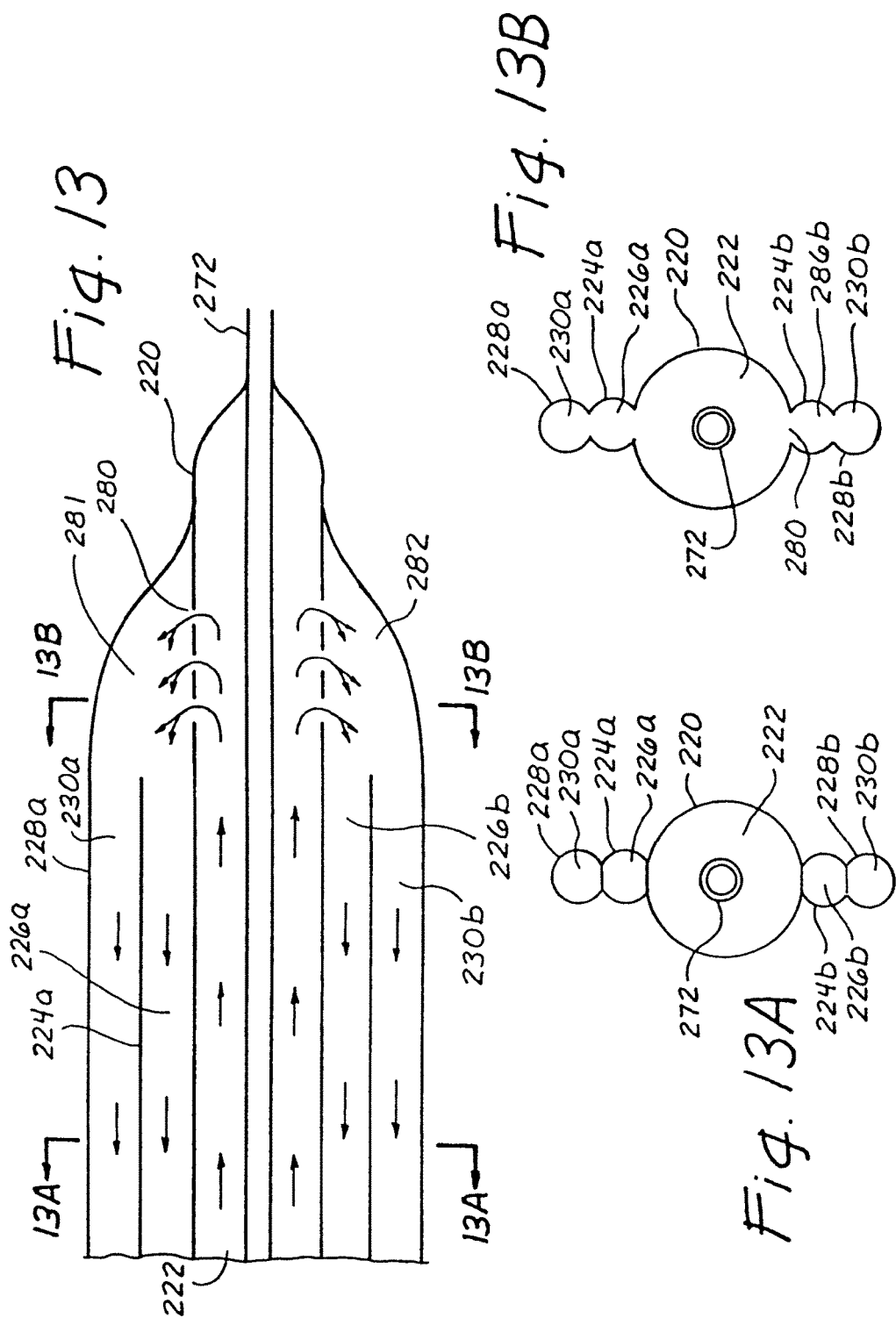

INHIBITION OF PLATELET ACTIVATION, AGGREGATION AND/OR ADHESION BY HYPOTHERMIA

RELATED APPLICATIONS

This application is a continuation of U.S. patent application Ser. No. 13/868,764 filed Apr. 23, 2013 and issuing on Jun. 7, 2016 as U.S. Pat. No. 9,358,153, which is a continuation of U.S. patent application Ser. No. 12/962,487 filed Dec. 7, 2010 and issued on Apr. 23, 2013 as U.S. Pat. No. 8,425,581, which is a continuation of U.S. patent application Ser. No. 11/501,442 filed Aug. 8, 2006 and issued on Dec. 7, 2010 as U.S. Pat. No. 7,846,193, which is a continuation of U.S. patent application Ser. No. 10/408,617 filed Apr. 7, 2003, now abandoned, which was a continuation of U.S. patent application Ser. No. 09/790,249 filed Feb. 21, 2001 and issued on Apr. 8, 2003 as U.S. Pat. No. 6,544,282, the entire disclosures of each such patent and patent application being hereby expressly incorporated herein by reference.

FIELD OF THE INVENTION

This invention relates generally to methods for medical treatment and more particularly to the intravascular application of hypothermia to treat acute coronary syndromes or other disorders that are treatable by inhibiting platelet activation and/or platelet aggregation and/or platelet adhesion.

BACKGROUND OF THE INVENTION

As used in this patent application the terms Aanti-platelet@ and Aplatelet inhibiting@ shall mean any inhibition of platelet activation and/or platelet aggregation and/or platelet adhesion.

Platelet activation, aggregation and/or adhesion are believed to play significant rolls in the pathogenesis of many vaso-occlusive disorders such as unstable angina, acute myocardial infarction, reocclusion of vessels following balloon angioplasty, transient ischemic attacks and strokes. Generally speaking, when a blood vessel becomes damaged, chemical agonists bind with certain binding sites on circulating platelets, causing the platelets to become activated. The types of blood vessel wall damage that can trigger platelet activation include perforation or injury to the vessel wall, progression of atherosclerotic plaque, the performance of some interventional procedure (e.g., angioplasty, atherectomy or stenting) which stretches the vessel wall or causes intimal tearing, or other causes. When activated, platelets interact with fibrinogen, fibronectin and other clotting factors causing them to adhere to the affected blood vessel wall and to aggregate with one another and with other blood cells (e.g., leukocytes). This activation, adherence and aggregation of platelets leads to the formation of a thrombus or blood clot.

Platelet inhibiting drug therapy (i.e., therapy that prevents or deters platelet activation and/or aggregation and/or adhesion) has been used in a wide variety of cardiovascular disease states. Some platelet inhibiting drugs, such as aspirin and ticlopidine (Ticlid™ Roche Laboratories, Inc., Nutley, N.J.) prevent platelet activation by inhibiting the agonists which cause the platelets to activate. However, each of these agonist-inhibitng drugs is largely specific to only one platelet activation pathway. For example, aspirin is believed to actively block platelet activation that occurs via a cyclooxygenase pathway but has little or no efficacy in blocking platelet activation that occurs via adenosine diphosphate (ADP). On the other hand, ticlopidine is effective in inhibiting platelet aggregation that occurs via ADP but has little or no efficacy in inhibiting platelet activation that occurs through the cyclooxygenase pathway. Other antiplatelet drugs, known as glycoprotein IIb/IIIa inhibitors, are thought to inhibit the activation of platelets by preventing binding sites located on the platelet membrane glycoprotein complex IIb/IIIa (GP IIb/IIIa) from becoming active even after the platelet has been triggered by an activation agonist. In this manner, the GP IIb/IIIa binding sites are rendered unavailable for binding with fibrinogen, fibronectin and other clotting factors, and as a result platelet aggregation, platelet adhesion or clot formation are inhibited. Examples of GP IIb/IIIa inhibitors include abciximab (ReoPro™, Centocor, Inc., Malvern, Pa.), eptifibatide (Integrilin™, COR Therapeutics, South San Francisco, Calif.) and tirofiban (Aggrast™, Merck & Co., West Point, Pa.).

One drawback associated with the use of antiplatelet drug therapy is that it can be expensive, especially when the newer glycoprotein IIb/IIIa inhibiting drugs are used. Also, as with virtually all drugs, the antplatelet drugs can cause side effects. Moreover, once antiplatelet drugs have been administered, the duration of their antiplatelet action can last for as long as four to six weeks. The resultant ongoing platelet inhibiting effect can be problematic in some cases, such as where some hemorrhage occurs or where a decision is made to subject the patient to surgery or some other invasive procedure, during or after which control of bleeding may be highly desirable. In this regard, as explained in the following paragraphs, the inability to rapidly reverse the effect of antiplatelet drugs can be particularly problematic in patients who suffer from certain acute cardiovascular require immediate treatment for acute coronary syndromes, such as unstable angina or non-Q wave myocardial infarction (MI), but who may subsequently be required to undergo cardiac surgery or another invasive procedure wherein control of bleeding is desirable.

Accute Coronary Syndromes: Unstable Angina and Non-Q Wave MI

Unstable angina, also referred to as Aaccelerating angina@, Anew-onset angina@ or Aprogressive angina@ is often characterized by a) chest pain that persists even in the absence of exercise, b) an increase in the severity, frequency, or duration of anginal chest pain, and/or c) the onset of anginal pain a lower levels of exercise than before. It has been reported that unstable angina occurs at some time in the lives of approximately 6 out of 10,000 people. Unstable angina typically arises in patient=s who have a history of stable or exercise induced angina due to the presence of atherosclerotic plaque in one or more of the patient=s coronary arteries. Non-Q-wave MI is a condition in which a blockage within a coronary artery causes a mild MI. A more serious MI often follows the occurrence of a non-q wave MI. In fact, patients who suffer from a non-Q wave MI are considered to be at even higher risk for death than individuals with unstable angina.

Both unstable angina and non-Q wave MI fall into a category of serious, life-threatening emergency conditions known as acute coronary syndromes. Both the onset of unstable angina and the occurrence of non-Q wave MI can be attributed to the rupture of a coronary atherosclerotic plaque. The rupture of the coronary atherosclerotic plaque in turn causes platelets to aggregate and blood clots to form, thereby converting the prior relatively stable narrowing of the coronary artery into an unstable ("high-grade") occlusion that severely limits blood flow to a region of the heart muscle, even when the patient is at rest.

Patients with acute coronary syndromes, such as unstable angina and non-Q wave MI, run a high risk of a fatal or non-fatal heart attack. These acute coronary syndromes require immediate hospitalization and the prompt administration of initial stabilizing treatment is a critical first step in preventing a possibly fatal heart attack from occurring. The goals of such initial stabilizing treatment is to reduce the severity of the acute symptoms and to prevent the situation from evolving into a full blown MI or potentially fatal cardiac arrhythmia. The immediate treatment often includes the administration of drugs that prevent or deter platelet aggregation or blood clotting, such as aspirin, heparin, or platelet inhibiting drugs as discussed in more detail herebelow as well as other agents such as nitroglycerin (often by paste or intravenously) beta-blockers, calcium channel blockers, antianxiety medications, and medications to control blood pressure and abnormal heart rhythms.

After the drug therapy has been initiated, the patient may be observed to determine if the condition will stabilize as a result of the aggressive medical management. If the patient does not stabilize, the patient will typically be evaluated to determine if CABG (coronary artery bypass grafting) surgery, PTCA (percutaneous transluminal coronary angioplasty) or some other surgical or interventional procedure is indicated. If surgery or an interventional procedure is indicated and the patient is otherwise a candidate for such surgery or intervention, the patient may then be taken to the catheterization lab for a PTCA or to the operating room for a CABG. In these patients the presence of previously administered platelet inhibiting drugs (i.e., drugs that inhibit platelet activation and/or aggregation and/or adhesion) can be a problem.

Transient Ischemic Attacks:

Another condition that may result from platelet activation, aggregation and/or adhesion is known as a transient ischemic attack (TIA). A TIA typically lasts from a few minutes to a few hours. TIAs are caused by interrupted blood flow to a part of the brain, resulting in neurologic symptoms such as slurred speech, dizziness, double vision, or weakness in a limb. The occurrence of a TIA indicates that the patient is at a significant risk of undergoing a full-blown ischemic stroke, potentially resulting in permanent brain damage or death. The rapid induction of platelet inhibition during or after the occurrence of a TIA may help to minimize the risk that the patient will suffer a full scale embolic stroke. However, after more definitive diagnostic tests are performed it may be determined that the patient is a candidate for an interventional or surgical procedure designed to alleviate blockages in the carotid or cerebral vasculature or that the cause of the patient=s symptoms is not, in fact, a TIA but rather a small localized area of bleeding in the patient=s brain. In such instances, it would be highly desirable to be able to cease or reverse any platelet inhibition therapy that has begun, but such cessation or reversal of the platelet inhibition may take as long as weeks (e.g., 4-6 weeks).

Thus, in view of the foregoing, there exists a need for the development of a platelet inhibiting treatment that may be rapidly administered to a patient who has suffered an acute coronary syndrome (unstable angina or non-Q wave MD or a TIA, but which can be rapidly discontinued or reversed if it is no longer indicated, such as when the patient is selected to undergo an invasive interventional or surgical procedure (e.g., PTCA or CABG) where a risk of untoward bleeding is identified.

SUMMARY OF THE INVENTION

The present invention provides a method for treating an acute coronary syndrome (i.e., unstable angina or non-Q-wave MD or TIA or otherwise causing platelet inhibition (i.e., prevention or deterrence of platelet activation and/or platelet aggregation and/or platelet adhesion) in a human or veterinary patient. In general, the method comprises the steps of a) diagnosing the acute coronary syndrome or other disorder wherein platelet inhibition is a desirable therapeutic objective, b) placing a heat exchange apparatus in heat exchange proximity with the patient=s blood and c) using the heat exchange apparatus to cool the patient=s blood to a temperature at which the desired platelet inhibition occurs. The heat exchange apparatus may be, for example a heat exchange catheter with a heat exchange region placed in the vasculature of the patient so that it directly exchanges heat with the blood flowing over the heat exchange region. Alternatively it may be a heat exchange catheter having a heat exchange region placed in the esophagus of a patient and exchange heat with blood in the aorta through the esophageal and aortic walls. It may even be be an enhanced method of cooling blood through the skin of the patient, provided that whatever heat exchange method is used is fast and efficient enough to effect a reduction of blood and tissue temperature sufficient to inhibit platelet activation sufficient for the thearapeutic use here described.

In humans, blood flowing in heat exchange proximity to the heat exchange apparatus may be cooled to a temperature of less than 36_C and typically in the range of 32_C to 36_C. The temperature of the blood and/or the target tissue will be reduced to therapeutically sufficent levels fairly fast, generally in less than 3 hours, and with intravascular hypothermia applied for the purpose of treating an acute coronary syndrome, typically less than 15 minutes after the catheter is placed and begins cooling. The patient=s blood may be maintained at the cooled temperature for any period of time desired, but typically such treatment will be maintained for a period of time from approximately 1 hour to approximately 3 days. Specifically, for patients being treated for unstable angina, the hypothermic treatment will typically be maintained for approximately 1 to 6 hours.

Further in accordance with the invention, the foregoing method of causing platelet inhibition may be performed in patient=s who are suffering from unstable angina, non-Q wave MI and/or TIA=s. The hypothermia-induced platelet inhibition caused by this method may be maintained until the patient either a) spontaneously stabilizes so as to cause platelet inhibition to be no longer indicated, b) becomes stabilized by medical therapy which may or may not include platelet inhibiting drugs and/or c) undergoes an interventional (e.g., PTCA, atherectomy, etc.) or surgical (CABG) procedure that obviates the need for continued platelet inhibition.

Further in accordance with the invention, the foregoing method of causing platelet inhibition by hypothermia may be performed as an alternative or stand-alone treatment or may be combined with other platelet inhibiting therapies or drugs, such as aspirin; non-steroidal antiinflamatories; ticlopidine; anticoagulants (e.g., heparin or warfarin); GP IIb/IIIa inhibitors (e.g., abcixmab or tirofiban) or any possible combination thereof. The hypothermic platelet inhibiting treatment of the present invention, when used in combination with platelet inhibiting drugs, may allow for a desirable reduction in the dosage(s) of the platelet inhibiting drugs used, thereby avoiding drug-related side effects or facilitation faster clearance and termination of the effect(s) of such drug(s) after cessation of drug treatment.

Further aspects and particulars of the present invention will become apparent to those of skill in the art upon reading and understanding of the detailed description and examples set forth herebelow.

BRIEF DESCRIPTION OF THE DRAWINGS

FIG. 1 is a perspective drawing of an embodiment of the catheter of the invention.

FIG. 1A is a perspective drawing of an alternative tie-down at the proximal end of the catheter shown in FIG. 1.

FIG. 2 is a cross-sectional drawing of the shaft of the catheter taken along the line 2-2 in FIG. 1.

FIG. 3 is a cross-sectional drawing of the heat exchange region of the catheter taken along the line 3-3 in FIG. 1.

FIG. 3A is a corss-sectional view through line 3A-3A of FIG. 1.

FIG. 4 is a perspective drawing of a segment of the heat exchange region of the catheter within the circle 4-4 in FIG. 1.

FIG. 5 is a cross-sectional drawing of the heat exchange region of the catheter taken along the line 5-5 in FIG. 1.

FIG. 6 is a perspective drawing of a segment of the heat exchange region of the catheter within the circle 6-6 in FIG. 1.

FIG. 7 is a perspective drawing of the multi-lobed balloon of one embodiment of the invention.

FIG. 8 is a perspective drawing of the distal portion of the shaft of one embodiment of the invention.

FIG. 10 is an expanded view of the attachment of the central lumen of the balloon to the shaft of the catheter of FIG. 9 showing the region within the circle 10-10 in FIG. 9.

FIG. 10 A is an expanded view of the plug between the shaft and the central lumen of the balloon of the catheter of FIG. 9 showing the region within the circle 10A-10A in FIG. 9.

FIG. 11 is a perspective view of a portion of a multi-lobed, curvilinear heat exchange balloon that forms a portion of one embodiment of the invention.

FIG. 11A is a cross sectional view of the heat exchange region taken along the line 11A-!!A in FIG. 11.

FIG. 12 is a sectional view of the proximal portion of the heat exchange region of one embodiment of the invention.

FIG. 12A is a cross-sectional view of a portion of the heat exchange region taken along the line 12A-12A of FIG. 12.

FIG. 12B is a cross-sectional view of a portion of the heat exchange region taken along the line 12B-12B of FIG. 12.

FIG. 12C is a cross-sectional view of a portion of the heat exchange region taken along the line 120-120 of FIG. 12.

FIG. 13 is a sectional view of the distal portion of the heat exchange region of one embodiment of the invention.

FIG. 13A is a cross-sectional view of a portion of the heat exchange region taken through line 13A-13A of FIG. 13.

FIG. 13B is a cross-sectional view of a portion of the heat exchange region taken through line 13B-13B FIG. 13.

DETAILED DESCRIPTION OF EXEMPLARY EMBODIMENTS

The following detailed description is provided for the purpose of describing only selected embodiments or examples of the invention and is not intended to describe all possible embodiments and examples of the invention.

A. General Method for Hypothermic Platelet Inhibition

Figure 9:
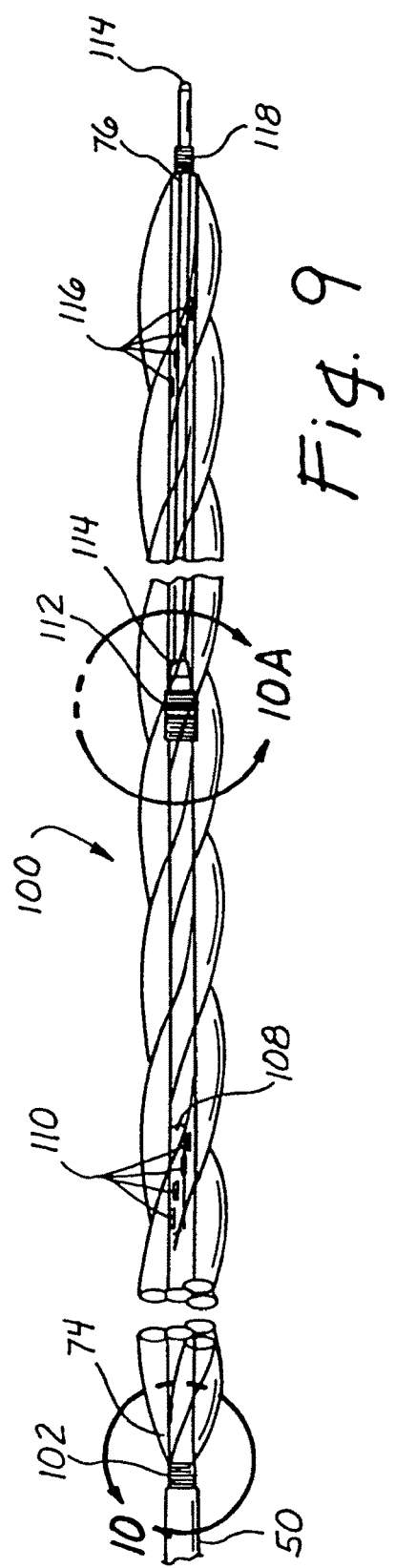
FIG. 9 is a perspective drawing, partially in ghost, of the heat exchange region formed by the shaft and multi-lobed balloon of FIGS. 7 and 8.
Figure 14:
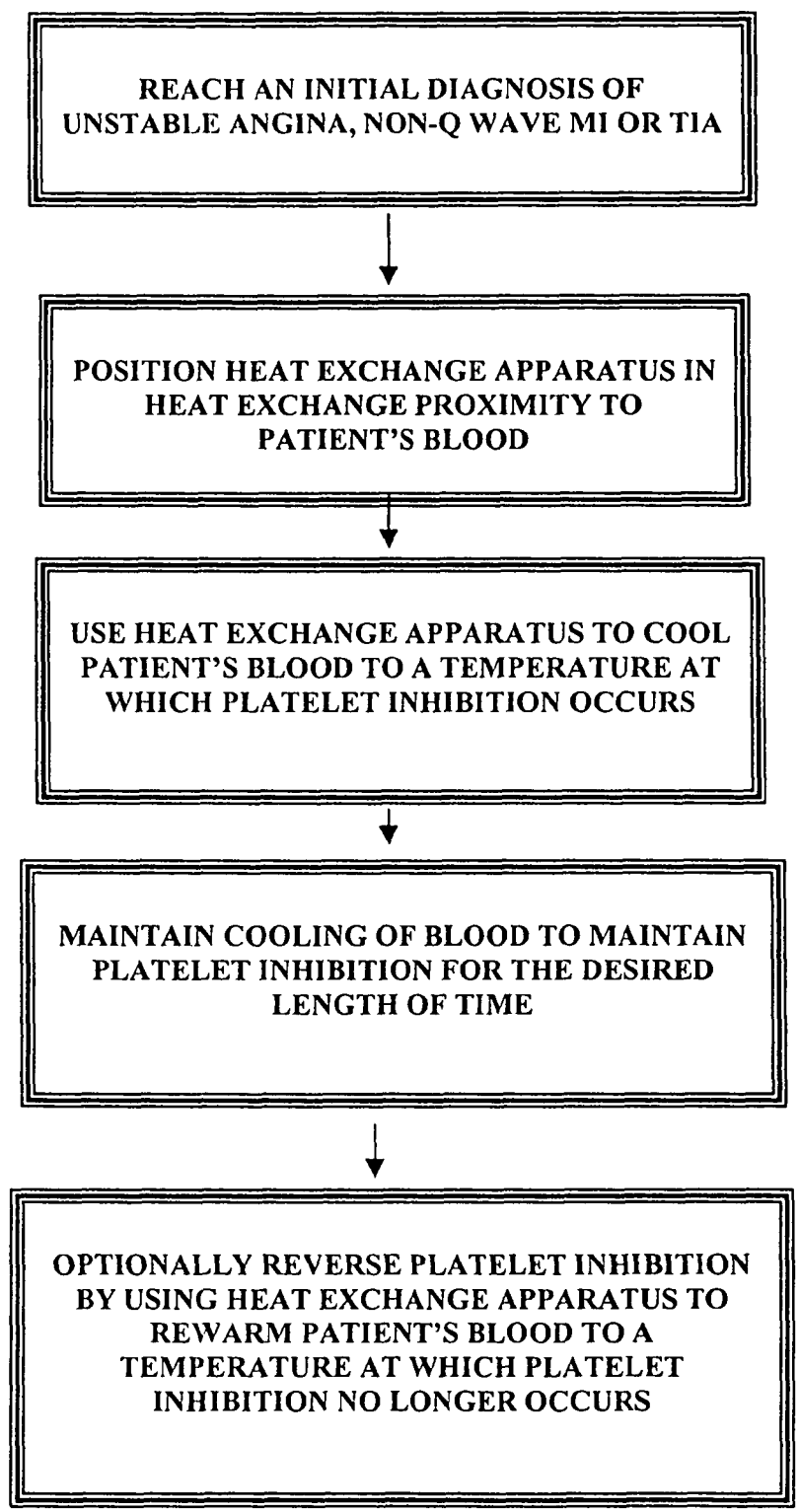
FIG. 14 is a general flow diagram of a platelet inhibition method of the present invention

FIG. 14 is a flow diagram which generally shows the manner in which the method of the present invention may be used in humans to cause platelet inhibition after an initial diagnosis or clinical impression of unstable angina, non-Q-wave MI, transient ischemic attack (TIA) or other disorder wherein platelet inhibition is desired, has been reached. As used herein the term platelet inhibition means any or all of; a) prevention or deterrence of platelet activation, b) prevention or deterrence of platelet adhesion and/or c) prevention or deterrence of off platelet aggregation. As shown in FIG. 14, after the initial diagnosis or clinical impression has been reached, the next step of the general method is to position a heat exchange apparatus in heat exchanging proximity with the blood of the human or veterinary patient. This step may be accomplished as described above, with any effective method having adequate speed and efficiency but is preferably effected by percutaneously inserting and transluminally advancing a heat exchange catheter, heat exchange probe or other or elongate heat exchanging member into a blood vessel, for example the inferior vena cava (IVC). Typically the heat exchanging member will be a flexible catheter which has a heat exchanger or heat exchange region located at or near its distal end. However, it will be appreciated that various other elongate, percutaneously insertable, transluminally advanceable heat exchange apparatus may be employed. In general, examples of heat exchange catheters and related devices & controllers that are useable in this step of the method are described in PCT International Application No, PCT/US99/18939 and U.S. Pat. No. 5,486,208 (Ginsburg), U.S. Pat. No. 5,149,676 (Ginsburg), U.S. Pat. No. 6,149,673 (Ginsburg), U.S. Pat. No. 5,174,285 (Fontenot), U.S. Pat. No. 5,344,436 (Fontenot, et al.), U.S. Pat. No. 5,957,963 (Dobakl II), U.S. Pat. No. 6,096,608 (Dobak II, et al.) and U.S. Pat. No. 6,126,684 (Gobin, et al.), the entire disclosures of which expressly incorporated herein by reference. In particular, one presently preferred intravascular heat exchange catheter system for use in the present invention is described in U.S. Provisional Application No. 60/181, 249 the entirety of which is expressly incorporated herein by reference and portions of which are set forth in the paragraphs herebelow.

With further reference to FIG. 14, the second general step of the method may be to use a heat exchange apparatus that had been positioned in the patient=s vasculature to cool the patient=s blood to a temperature at which platelet inhibition (i.e., inhibition of platelet activation and/or aggregation and/or adhesion) occurs. It has previously been established that hypothermia can inhibit platelet activation and aggregation. see, Michelson, A. D., et. al., Reversible Inhibition of Human Platelet Activation by Hypothermia In Vivo and In Vitro, Thromb Haemost 71 (5): 633-40 (1994) However, hypothermia-induced platelet inhibition is not known to have been previously used as a means for treating acute coronary syndromes (unstable angina or non Q-wave MI) or TIAs. Nor has it been known to use an intravascular heat exchange apparatus to effect hypothermia for the purpose of inhibiting platelet activation, aggregation or adhesion.

Furthermore, as shown in FIG. 14, purposeful and relatively rapid reversal of the hypothermia-induced platelet inhibition may be accomplished by re-warming the patient. This re-warming of the patient may be carried out using the same intravascular heat exchange catheter as was used to previously cool the patient. It is not believed to have been heretofore known to use re-warming of a patent to reverse platelet inhibition for a therapeutic purpose, especially when such re-warming is performed using the same heat exchange device and particularly the same intravascular heat exchange device as had previously been used to cool that patient.

The use of the intravascular heat exchange apparatus in the present invention generally permits hypothermia to be induced more rapidly and with substantially greater control than by noninvasive means such as wrapping the patient in a hypothermia blanket. The temperature to which the patient is cooled to effect the desired platelet inhibition is typically below about 36_C, and preferably in the range of approximately 32 to 36_C. In this invention, either whole-body hypothermia or partial-body hypothermia may be used. When whole-body hypothermia is used, the patient=s core body temperature may be monitored and maintained at the desired platelet inhibition temperature. When partial-body hypothermia is used the temperature of a desired organ, limb or anatomical portion of the body will be monitored and maintained at the desired platelet inhibition temperature. Concurrently with the hypothermia, the patient may be anesthetized or may receive medications or other therapy to prevent or lessen shivering or discomfort due to the hypothermia. Examples of medications that may be administered to minimize shivering or discomfort during the hypothermic treatment are described in POT International Application No, PCT/US00/20321. The specific drugs used to prevent shivering may include meperidine, buspirome, dexmedetomidine and/or combinations thereof. In the alternative, where it is undesirable to administer anti-shivering drugs, the patient=s body temperature may be maintained blow normothermia (to achieve some platelet inhibition) but above the shivering threshold, which is typically about 35-35.5_C.

In accordance with the invention hypothermia may be administered as the sole platelet inhibition treatment, at least for a period of time sufficient to allow physicians to fully evaluate the patient=s condition and to reach an appropriate decision regarding the initiation of platelet inhibiting drug therapy. In other instances, it may be desirable to administer intravascular hypothermia in accordance with this invention concurrently with the administration of platelet inhibiting drugs or other platelet inhibiting therapies so as to speed the onset of the desired platelet inhibiting effect, to reduce the dosages of platelet inhibiting drugs or other platelet inhibiting therapies required, or to otherwise improve the efficacy or reduce the toxicity of the platelet inhibiting treatment being used.

The application of hypothermia in accordance with this invention may, in addition to effecting direct platelet inhibition, simultaneously reduce overall tissue damage to an affected region. For example it may reduce blood vessel wall inflammation or microvascular injury thought to serve as a focal point for adhesion of platelets or thrombus formation. This antiinflamatory or vessel-wall-protecting effect that accompanies the anti-platelet effect of intravascular hypothermia may not be realized with anti-platelet drug therapy alone. Further, the application of hypothermia may, simultaneously with reduction of platelet inhibition, protect the target tissue in other ways. For example, hypothermia has been found to be generally myoprotective (i.e., protective of muscle cells against damage from insults like hypothermia or ischemia) and if intravascular hypothermia is applied to the blood in the IVC immediately before the blood enters the heart, it might simultaneously provide protection against damage by platelet activation and provide protection against damaging chemical cascades such as repurfusion damage to cell membranes. Likewise, hypothermia has been shown to be generally neuroportective, and if anti-platelet hypothermia is applied as a treatment for TIA=s, the hypothermia might simultaneously protect the brain tissue against damage by excitatory amino acids, destructive free radicals and the like in addition to the protection for the direct damage done by activated platelets.

B. A Preferred Intravascular Heat Exchange Catheter System

Referring to FIGS. 1 through 10A, in one embodiment, the catheter is comprised of a shaft 50 with a heat exchange region 100 thereon. The shaft has two roughly parallel lumens running through the proximal shaft, an inflow lumen 52 and an outflow lumen 54. The shaft generally also comprises a working lumen 56 running therethrough for the insertion of a guide wire, or the application of drugs, radiographic dye, or the like to the distal end of the catheter. The heat exchange region comprises a four-lumen balloon, with three outer lumens 58, 60, 62 disposed around an inner lumen 64 in a helical pattern. In the particular embodiment shown, the balloon preferably makes one full rotation about the inner lumen 64 for each 2 to 4 inches of length. All four lumens 58, 60, 62 and 64 are thin walled balloons and each outer lumen 58, 60, 62 shares a common thin wall segment 66, 68, 70 with the inner lumen. The balloon is approximately twenty-five centimeters long, and when inflated has an outer circumference 72 of approximately 0.328 in. When deflated, the profile is generally about 9 French (3 French is 1 mm in diameter). When the balloon portion is installed on the shaft, both the proximal end 74 of the balloon and the dital end 76 of the balloon are sealed around the shaft in fluid tight seals, as described more fully hereabelow. Heat exchange fluid may be directed in through the inflow lumen, return through the outer lobes of the balloon in heat exchange proximity with blood flowing over the outside of the balloon, and then out through the outflow lumens, as will be described in greater detail below.

The catheter is attached at its proximal end to a hub 78. At the hub, the guide wire lumen 56 communicates with a guide wire port 80, the inflow lumen 52 is in fluid communication with an inflow port 82, and the outflow lumen 54 is in communication with an outflow port 84. Attached at the hub and surrounding the proximal shaft is a length of strain relief tubing 86 which may be, for example, a length of heat shrink tubing. The strain relief tubing may be provided with suture tie-downs 88, 90. Alternatively, a butterfly tie-down 92 may be provided. (See FIG. 1A).

Between the strain relief tubing 86 and the proximal end of the balloon 74, the shaft 50 is extruded with an outer diameter of about 0.118 inches. The internal configuration is as shown in cross-section in FIG. 2. Immediately proximal of the balloon attachment 74, the shaft is necked down 94. The outer diameter of the shaft is reduced to about 0.100 to 0.110 inches, but the internal configuration with the three lumens is maintained. Compare, for example, the shaft cross-section of FIG. 2 with the cross-section of the shaft shown in FIG. 3, This length of reduced diameter shaft remains at approximately constant diameter of about 0.100 to 0.110 inches between the necked down location at 94 and a distal location 96 where the outflow lumen is sealed and the guide wire extension tube 98 is attached as will be described.

At the necked down location 94, a proximal balloon marker band 102 is attached around the shaft. The marker band is a radiopaque material such as a platinum or gold band or radiopaque paint, and is useful for locating the proximal end of the balloon by means of fluoroscopy while the catheter is within the body of the patient.

At the location marked by the marker band, all four lobes of the balloon are reduced down and fastened around the inner member 67 in a fluid-tight seal. This may be accomplished by folding the outer lobes of the balloon 58, 60, 62 down around the inner lumen 64, placing a sleeve, for example a short length of tubing, snuggly over the folded-down outer lumens of the balloon and inserting adhesive, for example by wicking the adhesive, around the entire inner circumference of the sleeve. The inner lumen is then fastened to the shaft using a second short length of tubing. The second short length for example 1 mm, of intermediate tubing 104 is heat welded to the inside of the inner lumen. The intermediate tube has an outer diameter approximately the same as the inner diameter of the inner lumen. The intermediate tube is then slid over the shaft at about the location of the neck-down region near the proximal marker 102, and adhesive 106 is wicked into the space between the inside of the intermediate tubing and the outer surface of the shaft 50. A similar process may be used to attach the distal end of the balloon, as will be described, except that the distal end of the balloon is attached down around the guide wire extension tube 98 rather than the shaft.

Just distal of the proximal balloon seal, under the balloon within the inner lumen, an elongated window 108 is cut through the wall of the outflow lumen in the shaft. Along the proximal portion of the balloon above this window, five slits, e.g. 110, are cut into the common wall between each of the outer lumens 58, 60, 62 and the inner lumen 64. Because the outer lumens are twined about the inner lumen in a helical fashion, each of the outer tubes passes over the outflow lumen of the inner shaft member at a slightly different location along the length of the inner shaft and, therefore, an elongated window 108 is cut into the outflow lumen of the shaft so that each outer lumen has at least one slit e.g. 110 that is located over the window in the shaft. Additionally, there is sufficient clearance between the outer surface of the shaft and the wall of the inner lumen to allow relatively unrestricted flow of heat exchange fluid through all 5 slits in each outer lumen, around the shaft, and through the elongate window 108 into the outflow lumen 54 in the shaft 50.

Distal of the elongated window in the outflow lumen, the inner lumen 64 of the four-lumen balloon is sealed around the shaft in a fluid tight plug. Referring to FIG. 10a, the plug is formed by, for example shrinking a relatively thick length of PET tubing to form a length of plug tubing 112 where the inner diameter of the length of plug tubing is approximately the same as the outer diameter of the shaft at the location where the plug is to be formed. The plug tubing is slid over the shaft and fits snugly against the shaft. The shaft is generally formed of a material that is not heat shrinkable. As may be seen in FIG. 10A and FIG. 3, some clearance exists between the outer wall of the shaft and the inner wall of the inner lumen 64. The walls of the inner lumen are composed of thin heat shrinkable material, for example PET. A probe with a resistance heater on the distal end of the probe is inserted into the guide wire lumen of the shaft and located with the heater under the plug tubing. The probe is heated, causing the heat shrink wall of the inner lumen to shrink down against the plug tubing, and the plug tubing to shrink slightly down against the shaft. The resultant mechanical fit is sufficiently fluid tight to prevent the outflow lumen and the space between the shaft and the wall of the inner lumen from being in fluid communication directly with the inner member or the inflow lumen distal of the plug except through the outer lumens as will be detailed below.

Just distal of the plug, the outflow lumen is closed by means of a heat seal 99, and the inflow lumen is skived to form an opening 101 to the inner member. This may be accomplished by necking down the shaft at 96, attaching a guide wire extension tube 98 to the guide wire lumen, and simultaneously opening the inflow lumen 101 to the interior of the inner lumen and heat sealing the outflow lumen shut 101. The guide wire extension tube continues through the inner lumen, beyond the distal seal of the balloon (described below) to the distal end of the catheter 114 and thereby creates communication between the guide wire port 80 and the vessel distal of the catheter for using a guide wire to place the catheter or for infusing drugs, radiographic dye, or the like beyond the distal end of the catheter.

The distal end of the balloon 76 is sealed around the guide wire extension tube in essentially the same manner as the proximal end 74 is sealed down around the shaft. Just proximal of the distal seal, five slits 116 are cut into the common wall between each of the three outer lumens 58, 60 62 of the balloon and the inner lumen 64 so that each of the outer lumens is in fluid communication with the inner lumen.

Just distal of the balloon, near the distal seal, a distal marker band 118 is placed around the guide wire extension tube. A flexible length of tube 120 may be joined onto the distal end of the guide wire tube to provide a soft tip to the catheter as a whole.

In use, the catheter is inserted into the body of a patient so that the balloon is within a blood vessel, for example in the inferior vena cava (NC), Heat exchange fluid is circulated into the inflow port 82, travels down the inflow lumen 52 and into the inner lumen 64 distal of the plug tube 112. The heat exchange fluid fills the inner lumen and travels down the inner lumen, thence through slits 116 between the inner lumen 64 and the three outer lumens 58, 60, 62.

The heat exchange fluid then travels back through the three outer lumens of the balloon to the proximal end of the balloon. Since outer lumens are wound in a helical pattern around the inner lumen, at some point along the length of the balloon near the proximal end and proximal of the plug, each outer lumen is located over the portion of the shaft having the window to the outflow lumen 108. There is also sufficient clearance between the wall of the inner lumen and the shaft, as illustrated in FIG. 3, that even the slits that are not directly over the window 108 allow fluid to flow into the space between the wall of the inner lumen and the outer wall of the shaft 50 and then through the window 108 and into the outflow lumen. The heat exchange fluid then flows down the outflow lumen and out the outflow port 84. At a fluid pressure of 41 pounds per square inch, flow of as much as 500 milliliters per minute may be achieved with this design.

Counter-current circulation between the blood and the heat exchange fluid is highly desirable for efficient heat exchange between the blood and the heat exchange fluid. Thus if the balloon is positioned in a vessel where the blood flow is in the direction from proximal toward the distal end of the catheter, for example if it were placed from the femoral vein into the Inferior Vena Cava (IVC) cava, it is desirable to have the heat exchange fluid in the outer balloon lumens flowing in the direction from the distal end toward the proximal end of the catheter. This is the arrangement described above. It is to be readily appreciated, however, that if the balloon were placed so that the blood was flowing along the catheter in the direction from distal to proximal, for example if the catheter was placed into the IVC from a jugular insertion, it would be desirable to have the heat exchange fluid circulate in the outer balloon lumens from the proximal end to the distal end. Although in the construction shown this is not optimal and would result is somewhat less effective circulation; this could be accomplished by reversing which port is used for inflow direction and which for outflow.

Where heat exchange fluid is circulated through the balloon that is colder than the blood in the vessel into which the balloon is located, heat will be exchanged between the blood and the heat exchange fluid through the outer walls of the outer lumens, so that heat is absorbed from the blood. If the temperature difference between the blood and the heat exchange fluid (sometimes called A_@), for example if the blood of the patient is about 37_C. and the temperature of the heat exchange fluid is about 0_C, and if the walls of the outer lumens conduct sufficient heat, for example if they are of very thin (0.002 inches or less) plastic material such as polyethylene terephthalate (PET), enough heat may be exchanged (for example about 200 watts) to lower the blood temperature sufficiently to effect hypothermic anti-platelet activity, and to cool the temperature downstream of the catheter, for example of the heart, sufficiently for therapeutic inhibition of platelet activation, aggregation and/or adhesion. If the cooling catheter is left in place long enough for example for over half an hour, the entire body temperature of the patient may be cooled sufficiently for hypothermic anti-platelet activity. In this way, for example, blood to the brain and even the brain tissue itself may be cooled sufficiently for therapeutic hypothermic anti-platelet effect.

The helical structure of the outer lumens has the advantage over straight lumens of providing greater length of heat exchange fluid path for each length of the heat exchange region. This creates additional heat exchange surface between the blood and the heat exchange fluid for a given length of balloon. It may also provide for enhanced flow patterns for heat exchange between flowing liquids. The fact that the heat exchange region is in the form of an inflatable balloon also allows for a minimal insertion profile, for example 9 French or less, while the heat exchange region may be inflated once inside the vessel for maximum diameter of the heat exchange region in operation.

Automated control of the process is optional. Examples of apparatus and techniques that may be used for automated control of the process are described in U.S. Pat. Nos. 6,149,676 and 6,149,676 and co-pending U.S. patent application Ser. No. 09/138,830, the entireties of which are expressly incorporated herein by reference.

Referring now to FIGS. 11 through 13B, in another example of a preferred embodiment, the heat exchange region is in the form of a series of five lumens arranged side-by-side in a configuration that may be loosely described as a twisted ribbon. The heat transfer fluid circulates to and from the heat exchange region 202 via channels formed in the shaft 206 in much the same manner as previously described for shaft 50. Indeed, although not depicted, the shaft has a similar internal configuration as the shaft previously described with an inflow lumen, an outflow lumen, and a working lumen. Although also not depicted, a hub is attached at the proximal end of the shaft which is maintained outside the body; the hub has a guide wire port communicating with the working lumen, an inflow port communicating with the inflow lumen, and an outflow port communicating with the outflow lumen. Heat exchange fluid is directed into the catheter through the inflow port and removed from the catheter through the outflow port. A guide wire, or alternatively medicaments, radiographic fluid or the like are introduced through the guide wire port and may thus be directed to the distal end of the catheter.

FIGS. 11 and 11A illustrate this embodiment of a heat exchange region 202 comprising a plurality of tubular members that are stacked in a helical plane. More specifically, a central tube 220 defines a central lumen 222 therewithin. A pair of smaller intermediate tubes 224a, 224b attaches to the exterior of the central tube 220 at diametrically opposed locations. Each of the smaller tubes 224a, 224b defines a fluid lumen 226a, 226b therewithin. A pair of outer tubes 228a, 228b attaches to the exterior of the intermediate tubes 224a, 224b in alignment with the aligned axes of the central tube 220 and intermediate tubes 224a, 224b. Each of the outer tubes 228a, 228b defines a fluid lumen 230a, 230b within, By twisting the intermediate and outer tubes 224a, 224b, 228a, 228b around the central tube 220, the helical ribbon-like configuration of FIG. 11 is formed.

Now with reference to FIGS. 12 and 12A-12C, a proximal manifold of the heat exchange region 202 will be described. The shaft 206 extends a short distance, desirably about 3 cm, within the central tube 220 and is thermally or adhesively sealed to the interior wall of the central tube as seen at 250. As seen in FIG. 12A, the shaft 206 includes a planar bulkhead or web 252 that generally evenly divides the interior space of the shaft 206 into an inflow lumen 254 and an outflow lumen 256. A working or guide wire lumen 260 is defined within a guide wire tube 262 that is located on one side of the shaft 206 in line with the bulkhead 252. Desirably, the shaft 206 is formed by extrusion. The outflow lumen 256 is sealed by a plug 264 or other seal at the terminal end of the shaft 206. The inflow lumen 254 remains open to the central lumen 222 of heat exchange region 202. The guide wire tube 262 continues a short distance and is heat bonded at 270 to a guide wire extension tube 272 generally centered within the central tube 220.

A fluid circulation path is illustrated by arrows in FIG. 12 and generally comprises fluid passing distally through the inflow lumen 254 and then through the entirety of the central lumen 222. The heat exchange fluid is directed from the central lumen 222 to the intermediate and outer tubes as will be described below, and returns through the lumens 226a, 226b, and 230a, 230b of the intermediate and outer tubes 224a, 224b, and 228a, 228b, respectively, and enters reservoirs 274 and 275. Alternatively, two windows may be formed 276 and a counterpart not shown in FIG. 12 one helical twist farther down the shaft, between each side of the twisted ribbon (i.e., lumens 224a and 224b on one side, and 228a and 228b on the other side). In this way, one reservoir from each side of the twisted ribbon is formed in fluid communication with the outflow lumen 256 (configuration not shown). Fluid then enters the outflow lumen 256 through apertures, e.g., 276, provided in the central tube 220 and a longitudinal port 278 formed in the wall of the shaft.

A distal manifold of the heat exchange region 202 is shown and described with respect to FIGS. 13 and 13A-13B. The outer tubes 228a, 228b taper down to meet and seal against the central tube 220 which, in turn, tapers down and seals against the guide wire extension tube 272. Fluid flowing distally through the central lumen 222 passes radially outward through a plurality of apertures 280 provided in the central tube 220. The apertures 280 open to a distal reservoir 282 in fluid communication with lumens 226a, 226b, and a distal reservoir 281 in fluid communication with lumens 230a, 230b of the intermediate and outer tubes 224a. 224b, and 228a, 228b.

With this construction, heat exchange fluid introduced into the input port 240 will circulates through the inflow lumen 254, into the central lumen 222, out through the apertures 280, and into the distal reservoir 282. From there, the heat exchange fluid will travel proximally through both intermediate lumens 226a, 226b and outer lumens 230a, 230b to the proximal reservoirs 274 and 275. Fluid then passes radially inwardly through the apertures 276 and port 278 into the outflow lumen 256. Then the fluid circulates back down the shaft 206 and out the outlet port 242.

The ribbon configuration of FIGS. 11-13B is advantageous for several reasons. First, the relatively flat ribbon does not take up a significant cross-sectional area of a vessel into which it is inserted. The twisted configuration further prevents blockage of flow through the vessel when the heat exchange region 202 is in place. The helical configuration of the tubes 224a, 224b, 228a, 228b also aids to center the heat exchange region 202 within a vessel by preventing the heat exchange region from lying flat against the wall of the vessel along any significant length of the vessel. This maximizes heat exchange between the lumens and the blood flowing next to the tubes. Because of these features, the twisted ribbon configuration is ideal for maximum heat exchange and blood flow in a relatively small vessel such as the carotid artery. As seen in FIG. 11A, an exemplary cross-section has a maximum diameter of about 5 mm, permitting treatment of relatively small vessels. The helical pattern of the balloon in the fluid flow may act to induce a gentle mixing action of the flowing blood to enhance heat exchange between the heat exchange surface and the blood without inducing hemolytic damage that would result from more violent churning action.

The deflated profile of the heat exchange region is small enough to make an advantageous insertion profile, as small as 7 French for some applications. Even with this low insertion profile, the heat exchange region is efficient enough to adequately exchange heat with blood flowing past the heat exchange region to alter the temperature of the blood sufficient for anti-platelet action and affect the temperature of tissue downstream of the heat exchange region. Because of its smaller profile, it is possible to affect the temperature of blood in smaller vessels and thereby provide treatment to more localized body areas.

This configuration has a further advantage when the heat exchange region is placed in a tubular conduit such as a blood vessel, especially where the diameter of the vessel is approximately that of the major axis (width) of the cross section of the heat exchange region. The configuration tends to cause the heat exchange region to center itself in the middle of the vessel. This creates two roughly semicircular flow channels within the vessel, with the blood flow channels divided by the relatively flat ribbon configuration of the heat exchange region. It has been found that the means for providing maximum surface for heat exchange while creating minimum restriction to flow is this configuration, a relatively flat heat exchange surface that retains two approximately equal semi-circular cross-sections. This can be seen in reference to FIG. 11A if the functional diameter of the dashed circle 300 is essentially the same as the luminal diameter of a vessel into which the twisted ribbon is placed. Two roughly semi-circular flow paths 302, 304 are defined by the relatively flat ribbon configuration of the heat exchange region, i.e. the width or major axis (from the outer edge of 228a to the outer edge of 228b) is at least two times longer than the height, or minor axis (in this example, the diameter of the inner tube 222) of the overall configuration of the heat exchange region. It has been found that if the heat exchange region occupies no more than about 50% of the overall cross-sectional area of the circular conduit, a highly advantageous arrangement of heat exchange to flow is created. The semi-circular configuration of the cross-section of the flow channels is advantageous in that, relative to a round cross-sectioned heat exchange region (as would result from, for example, a sausage shaped heat exchange region) the flow channels created minimize the surface to fluid interface in a way that minimizes the creation of laminar flow and maximizes mixing. Maximum blood flow is important for two reasons. The first is that flow downstream to the tissue is important, especially if there is obstruction in the blood flow to the tissue. The second reason is that heat exchange is highly dependent on the rate of blood flow past the heat exchange region, with the maximum heat exchange occurring with maximum blood flow, so maximum blood flow is important to maximizing heat transfer.

C. A Preferred Method for Hypothermic Treatment of Acute Corona Syndromes

FIG. 14 is a flow chart that generally depicts the use of hypothermia to treat unstable angina, non-Q wave MI or TIA=s by application of anti-platelet hypothermia. Once the diagnosis is made, a heat exchange apparatus is placed in heat exchange proximity with the patient=s blood. In many cases, that will be the placement of an intravascular catheter having a heat exchange region placed in the IVC, but may be any other means that is fast and effective enough to accomplish anti-platelet hypothermia. For example, if a surface cooling apparatus is placed in heat exchange proximity to the patient=s blood in the patient=s skin, that may suffice to exchange sufficient heat with the blood but generally only if the normal thermoregulatory defenses such as vasoconstriction are defeated so that effective heat transfer could occur, and the body=s normal thermoregulatory defense of generating heat through shivering is sufficiently disabled that the adequate cool temperature can be reached.

Once a hypothermic state capable of causing the desired anti-platelet effect (i.e., inhibition of platelet activation and/or aggregation and/or adhesion) is reached, it may be maintained by continued heat exchange with the patient=s blood at the precise amount to maintain a desired temperature. This may be accomplished by means of sensing the patient=s core temperature and removing more heat if the temperature begins to rise, or removing less heat if the temperature begins to fall below the desired level. Means of accomplishing this temperature maintanence with an intravascular heat exchange catheter are set out in U.S. Pat. Nos. 6,149,676 and 6,149,676, both to Ginsburg which are incorporated herein in full, and also in PCT International Application No. PCT/US99/18939 to Ginsburg et al, previously incorporated.

When it is desired to restore the patient to normal platelet activity, the platelet inhibition may be reversed, either by allowing the patient to become normothermic or optionally by rewarming the blood, perhaps with the same heat exchange apparatus that was used to induce the anti-platelet hypothermia.

Figure 15:
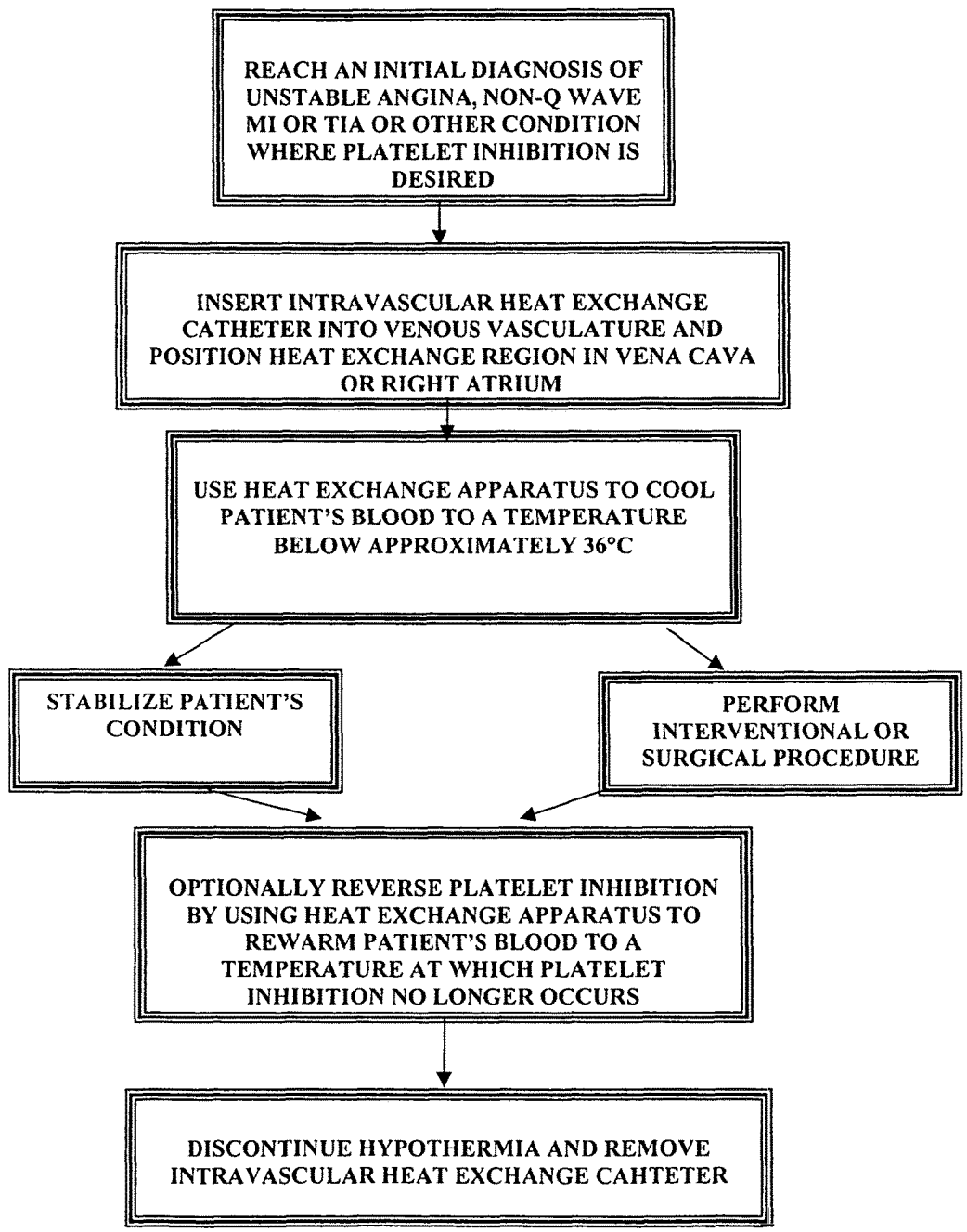
FIG. 15 is a flow diagram of a method for treating an acute coronary syndrome (e.g., unstable angina or non-Q wave MI) or TIA in accordance with the present invention.

FIG. 15 shows a flow diagram of a more specific, presently preferred method for using intravascular hypothermia to induce platelet inhibition (as defined herein) in a human patient who suffers from some condition wherein platelet inhibition is desired such as an acute coronary syndrome such as unstable angina or non-Q wave MI.

Typically, the patient will be assessed in a hospital emergency room or physician=s office and an initial diagnosis or clinical impression of unstable angina or non-Q wave MI will be made. Promptly after the diagnosis or clinical impression of unstable or non-Q wave MI has been reached, an intravascular heat exchange catheter, a such as (for example) the catheter 100 shown in FIG. 1, will be percutaneously inserted into a vein such as the femoral vein and advanced through the venous vasculature until the heat exchange region of the catheter 100 becomes positioned within the patient=s thorax in the inferior vena cava, superior vena cava or right atrium. A chest x-ray or other appropriate imaging study may be performed to verify the proper positioning of the catheter 100 and it will be appreciated that radio-opaque markers or other imageable markers may be formed all on or near the catheter=s heat exchange region to facilitate verification that the heat exchange region has been properly positioned. Thereafter, the heat exchange region of the catheter 100 will be cooled, for example by circulating cold heat exchange fluid through the interior of the heat exchange balloon Such circulation of cooled heat exchange fluid through the heat exchanger will cause venous blood which flows through the vena cava or right atrium to become cooled as it passes in heat exchange proximity to the heat exchange region of the catheter 100. Temperature-measuring probes may be positioned on or in the patient=s body (e.g., in the patient=s esophagus, on the tympanic membrane, in the axillary region, in the rectum, in the patient=s blood stream at a location that is not within heat exchange proximity to the heat exchange region of the catheter 100 etc) to monitor the patient=s core body temperature. Circulation of cooled heat exchange fluid through the heat exchange region of the catheter will preferably continue until the patient=s core body temperature reaches a target temperature at which the desired platelet inhibition will occur. In this example, the patient is unanesthetized and has not been treated with antishivering drugs and, thus, a target temperature of approximately 35.5-36.5_C will be maintained. By maintaining the patient-s temperature above approximately 35.5_C severe shivering will most likely be avoided. It is to be appreciated, however, that the shivering threshold may vary from patient to patient or from time point to time point and, thus, it may be desirable to adjust the patient=s core temperature, as needed, to avoid severe shivering or discomfort. Alternatively, the patient may be anesthetized or medicated with anti-shivering medications as described herein. While the patient is maintained in a hypothermic state, the patient=s condition will be observed, cardiac enzymes may be monitored and appropriate diagnostic studies may be performed to determine the severity of the acute coronary syndrome or TIA that is ongoing. In at least some cases, especially those where the patient is being treated for an acute coronary syndrome, angiography studies or other pre-operative/pre-intervention assessments (e.g., imaging studies, diagnostic tests) may be performed while the patient is maintained in the hypothermic state. These assessment may then be used to determine whether the patient is a candidate for a catheter-based intervention (e.g., PTCA, stenting, atherectomy, thrombectomy) or cardiac surgical intervention (e.g., CABG). Thereafter, a decision may be made to send the patent to the catheterization laboratory or radiology suite for a catheter-based intervention, to the operating room for a surgical intervention. Alternatively, a decision may be made not to perform a catheter-based intervention or surgery and, instead, to begin drug treatment long term medical management of the patient=s condition. In any event, should a stroke or heart attack occur, the already present hypothermia may present some protection for the neural tissues and cardiac muscle tissue. Some patients in whom an acute cardiac syndromes are initially diagnosed will become stabilized spontaneously or with appropriate ongoing medical therapy (e.g., the ongoing oral or topical administration of anti-rhythmic agents, beta-blockers, anticoagulants and/or platelet inhibiting drugs). If the patient become stabilized spontaneously or via medical therapy, the patient may then be re-warmed to a normothermic temperature (i.e., approximately 37_C for most human patients) and the heat exchange catheter may be removed. Prior to or during the rewarming, appropriate antiplatelet drug therapy may be commenced and will be continued if a decision has been made to maintain the patient on ongoing oral drug therapy after the patient leaves the hospital. In patients who do not become stabilized spontaneously or by emergency medical therapy, it may be appropriate for the patient to undergo an interventional procedure (e.g., PTCA, stenting or atherectomy) or it may be appropriate for the patient to undergo a cardiac surgical procedure (e.g., open or thoracoscopic CABG). Catheter-based interventional procedures like PTCA, stenting or atherectomy are typically performed in unanesthetized patients and, in those cases, it may be appropriate to continue the intravascular hypothermic treatment of the present invention during the performance of the catheter-based interventional procedure. Thereafter, if the interventional procedure has been successfully accomplished and the acute coronary syndrome is obviated, the intravascular hypothermic treatment may be discontinued and the heat exchange catheter removed. In patients who have received intravascular hypothermia as the sole platelet inhibiting treatment, the cessation of the hypothermia will also terminate the platelet inhibition and, therefore, post-procedure bleeding from the vascular access site at which the catheter(s) were inserted will not be complicated by ongoing platelet inhibition as may have occurred if non-reversible platelet inhibiting drugs had been administered prior to the interventional procedure.

In unstable angina patients that undergo cardiac surgical intervention such as CABG sometimes have hypothermia during surgery as the standard of care, often induced and maintained by a blood heat exchanger in the cardiopulmonary by pass machine. In such cases, hypothermic platelet inhibition may be administered to the patient prior to the patient going on the by-pass machine, and reversed by warming after the patient has been removed from the bypass machine.

In cardiac procedures where the patient is not placed on a cardiopulmonary by pass machine, hypothermic therapy has generally not been available. In such cases, however, the method of the present invention may be employed to provide platelet inhibition by administration of hypothermia, and subsequent reversal by re-warming by use of an intravascular heat exchange catheter as described above.

Although several illustrative examples of means for practicing the invention are described above, these examples are by no means exhaustive of all possible means for practicing the invention. The scope of the invention should therefore be determined with reference to the appended claims, along with the full range of equivalents to which those clams are entitled.

What is claimed is:

1. A method for causing temporary platelet inhibition in a human or veterinary patient in whom an initial diagnosis or clinical impression has been reached indicating that the patient suffers from an acute coronary syndrome, transient ischemic attack or other disorder that may benefit from therapeutic platelet inhibition, said method comprising the steps of:

placing an intravascular heat exchange apparatus within the vasculature of the patient; and, using the intravascular heat exchange apparatus to cool at least a portion of the patient's body to a temperature which causes platelet inhibition to occur and maintaining said temperature for a period of time, and, thereafter, rewarming said at least a portion of the patient's body to a temperature at which platelet inhibition is no longer caused to occur.

2. A method according to claim 1 wherein:
the intravascular heat exchange apparatus comprises a heat exchange catheter having a heat exchange region; and
the placing Step comprises inserting the heat exchange catheter into the vasculature of a patient and positioning said catheter so that the heat exchange region is in contact with blood flowing to the heart; and
the using Step comprises exchanging heat with the blood at the heat exchange region; and
said period of time comprises a time period sufficient to cause said platelet inhibition.

3. A method as in claim 1 wherein the said period of time is less than 4 hours.

4. A method according to claim 1 wherein said temperature which causes platelet inhibition to occur is below approximately 36° C. but greater than approximately 30° C.

5. A method according to claim 4 wherein the temperature which causes platelet inhibition to occur is between approximately 32° C. and approximately 34° C.

6. A method according to claim 1 wherein the intravascular heat exchange apparatus comprises an elongate flexible catheter that comprises a heat exchanger.

7. A method according to claim 6 wherein the heat exchanger of the catheter comprises less than the full length of the catheter that becomes placed in the patients vasculature.

8. A method according to claim 1 wherein the heat exchange apparatus is placed in the patient's venous vasculature.

9. A method according to claim 8 wherein the heat exchange apparatus is placed in the patient's vena cava.

10. A method according to claim 9 wherein the heat exchange apparatus is placed in the patient's inferior vena cava.

11. A method according to claim 9 wherein the heat exchange apparatus is placed in the patient's superior vena cava.

12. A method according to claim 1 wherein at least one surface projection is formed on the heat exchange apparatus to increase the effective heat exchange surface area of the heat exchange apparatus.

13. A method according to claim 12 wherein the at least one surface projection comprises a fin.

14. A method according to claim 13 wherein said fin comprises a raised area on at least a blood-contacting surface of the heat exchange apparatus.

15. A method according to claim 13 wherein said fin comprises a ridge.

16. A method according to claim 13 wherein said fin comprises a bulge.

17. A method according to claim 1 further comprising the steps of:
ceasing the use of the heat exchange apparatus to cool at least a portion of the patient's body; and,
removing the heat exchange apparatus from the patient's body.

18. A method according to claim 1 wherein the method is carried out in a patient who has been diagnosed with unstable angina.

19. A method according to claim 1 wherein the method is carried out in a patient who has been diagnosed with non-Q wave myocardial infarction.

* * * * *

UNITED STATES PATENT AND TRADEMARK OFFICE
CERTIFICATE OF CORRECTION

PATENT NO. : 10,369,044 B2
APPLICATION NO. : 15/174690
DATED : August 6, 2019
INVENTOR(S) : Dae et al.

Page 1 of 1

It is certified that error appears in the above-identified patent and that said Letters Patent is hereby corrected as shown below:

In the Claims

Column 17, Line 8, Claim 2, delete "Step" and insert -- step --

Column 17, Line 12, Claim 2, delete "Step" and insert -- step --

Signed and Sealed this
Third Day of November, 2020

Andrei Iancu
*Director of the United States Patent and Trademark Office*